(12) United States Patent  
Berger

(10) Patent No.: US 9,213,002 B2  
(45) Date of Patent: *Dec. 15, 2015

(54) APPARATUS AND METHOD FOR EVALUATING TIRE SELF-CLEANING CAPABILITY

(75) Inventor: Phillip A. Berger, Simpsonville, SC (US)

(73) Assignees: MICHELIN RECHERCHE et TECHNIQUE S.A., Granges-Paccot (CH); COMPAGNIE GENERALE DES ETABLISSEMENTS MICHELIN, Clermont-Ferrand (FR)

( * ) Notice: Subject to any disclaimer, the term of this patent is extended or adjusted under 35 U.S.C. 154(b) by 849 days.

This patent is subject to a terminal disclaimer.

(21) Appl. No.: 13/511,724

(22) PCT Filed: Nov. 25, 2009

(86) PCT No.: PCT/US2009/065849  
§ 371 (c)(1),  
(2), (4) Date: May 24, 2012

(87) PCT Pub. No.: WO2011/065943  
PCT Pub. Date: Jun. 3, 2011

(65) Prior Publication Data  
US 2012/0287269 A1 Nov. 15, 2012

(51) Int. Cl.  
*G01N 21/89* (2006.01)  
*B60C 11/00* (2006.01)  
*G01M 17/02* (2006.01)

(52) U.S. Cl.  
CPC ............ *G01N 21/8914* (2013.01); *B60C 11/00* (2013.01); *G01M 17/027* (2013.01)

(58) Field of Classification Search  
CPC .... G01M 17/013; G01M 17/012; G01M 1/34  
USPC ......................................................... 348/142  
See application file for complete search history.

(56) References Cited

U.S. PATENT DOCUMENTS 3,030,998 A 2/1960 Jensen  
3,817,306 A 6/1974 Sidles  
(Continued)

FOREIGN PATENT DOCUMENTS

DE 3546149 7/1986  
EP 0426457 5/1991  
(Continued)

OTHER PUBLICATIONS

European Search Report for EP0837308A3, dated Oct. 3, 1999.  
(Continued)

*Primary Examiner* — Sath V Perungavoor  
*Assistant Examiner* — Nathnael Aynalem  
(74) *Attorney, Agent, or Firm* — Dority & Manning, P.A.

(57) ABSTRACT

An apparatus and method for evaluating the ability of a tire to clean its tread is provided. For example, an apparatus (100) and method for evaluating the ability of a tire to eject materials such as e.g., mud from its tread during use is provided. Samples (10) of a subject test pattern are rotated at predetermined rpm profile. A camera (170) captures the effect of centrifugal forces on the materials during rotation, which in turn may be used to compare how differences in tread patterns impact the ejection of materials (15) from the tread during use.

18 Claims, 4 Drawing Sheets

(56) References Cited

U.S. PATENT DOCUMENTS

| | | | |
|---|---|---|---|
| 3,930,141 | A | 12/1975 | Koyama et al. |
| 5,016,696 | A | 5/1991 | Bonko et al. |
| 5,054,918 | A | 10/1991 | Downing |
| 5,113,688 | A * | 5/1992 | Lazeration ............ 73/8 |
| 5,153,899 | A * | 10/1992 | Curry ............... 378/61 |
| 5,174,151 | A * | 12/1992 | Adachi et al. ......... 73/146 |
| 5,347,588 | A | 9/1994 | Wilson |
| 5,357,799 | A | 10/1994 | Roth et al. |
| 5,777,219 | A | 7/1998 | Popio et al. |
| 5,900,531 | A * | 5/1999 | Mani et al. ............ 73/9 |
| 6,189,586 | B1 | 2/2001 | Guidry |
| 6,408,689 | B1 * | 6/2002 | Usami et al. .......... 73/146 |
| 6,536,490 | B2 | 3/2003 | Rooney |
| 6,986,372 | B2 | 1/2006 | Below |
| 2002/0177959 | A1 * | 11/2002 | Williams et al. ........ 702/41 |
| 2005/0034798 | A1 * | 2/2005 | Bright ............ 152/209.17 |

FOREIGN PATENT DOCUMENTS

| | | |
|---|---|---|
| EP | 0 837 308 A2 | 4/1998 |
| WO | WO 2005 018957 A2 | 3/2005 |

OTHER PUBLICATIONS

PCT International Search Report for PCT/US2009/065853, dated Sep. 3, 2010.

Wei, C.Z. Zhou, W.; Wang, Q.; Xinxin Li, "Monolithic pressure+acceleration sensor with self-test function for reliable & low-cost tire pressure monitoring system (TPMS) applications," Solid-State Sensors, Actuators, and Microsystems Conference (Transducers), 2011 16$^{th}$ International; pp. 1006, 1009, Jun. 5-9, 2011.

PCT International Search Report for PCT/US2009/065849, dated Sep. 3, 2010.

* cited by examiner

APPARATUS AND METHOD FOR EVALUATING TIRE SELF-CLEANING CAPABILITY

FIELD OF THE INVENTION

The present invention relates to the ability of a tire to clean its tread. More particularly, the present invention provides for evaluating the ability of a tire to eject materials such as e.g., mud from its tread during use.

BACKGROUND OF THE INVENTION

While many road surfaces are constructed from hardened surfaces such as asphalt or concrete, tires are also frequently used in "off road" applications such as mud, gravel, sand, compacted soil, and other surfaces where the material of the surface can become loaded into the tread pattern. For example, mud can fill part or all of the grooves or other features of a tread pattern as the tire rotates during use. As the grooves or other features fill and the tire becomes loaded with mud, traction can be adversely affected as the effective tire surface becomes slick. In such case, the vehicle may become immobile or stuck. However, if the tire can self-clean or remove these materials during rotation, then the tread features have an opportunity to provide traction and thereby move the vehicle. In an ideal construction, during each rotation the non-contacting portions of the tread would eject materials before rotating back into contact with the ground or road surface.

In addition to providing ornamental features attractive to the buyer, tread patterns may be developed for the purpose of improving traction in off road applications such as those mentioned above. In order to explore the self-cleaning efficacy of a proposed tread pattern, one or more tires can be constructed bearing the proposed pattern. In turn, these tires can then be placed on a test vehicle and subjected to various off road conditions in order to evaluate traction performance. Unfortunately, such an approach is expensive because e.g., a tire mold must be created or modified for each pattern change, the new tire must be manufactured, and then vehicle testing must be performed in off road conditions.

While it may be desirable to ultimately test each design on a vehicle in off road conditions, there exists a need for a generally less complex and less expensive option for testing the ability of various tread patterns to remove off road materials from grooves and other features of the patterns before subjecting a particular tread pattern to off road testing. Specifically, there is a need for an ability to test various design patterns for self-cleaning efficacy without necessarily building a complete tire for off road testing of each pattern or pattern change that is under consideration or development. A solution that provides for more rapid testing at less expense than prototype manufacture followed by off road testing would be very useful. A solution that can allow testing using only a portion of the entire tread pattern would also be particularly useful. These and other advantages are provided in one or more embodiments and aspects of the invention that will be described herein.

SUMMARY OF THE INVENTION

Objects and advantages of the invention will be set forth in part in the following description, or may be obvious from the description, or may be learned through practice of the invention.

In one exemplary embodiment of the present invention, a device for evaluating the removal of materials from a tire tread is provided. The device can include a mount configured for carrying the tread, a motor connected with the mount and adapted to rotate the mount about an axis of rotation so as to create centrifugal forces on the tread and materials in the tread; and a camera positioned to rotate in synchronization with the mount and configured to record images of the tread as the mount is rotated. The device can also include a controller in communication with the motor and configured for controlling the speed of rotation of the mount. A light source can be positioned adjacent to the mount for providing illumination of the tread. The camera may be connected to a camera eye that is positioned adjacent to the mount and directed towards the mount. The camera eye is connected to the camera and is configured to rotate in synchronization with the mount.

The apparatus may also include a plurality of aims connected with the motor, wherein the mount is attached to the end of one of the plurality of arms. A speed sensor can be provided for determining the speed at which the mount is rotated. The device can also include a carriage for receipt of the tire tread, the carriage being configured for removable connection with the mount.

In another exemplary aspect of the present invention, a method for evaluating the removal of materials from a tire tread is provided. The method can include loading a sample of the tread onto a testing device, rotating the sample at a predetermined rate using the testing device, recording images of the sample during the rotating step, and ejecting materials from the tread by centrifugal force during the rotating step. The images may be used to determine whether modifications to the tread sample will be made to effect the self-cleaning ability of the tread sample.

The method can also include a step of placing materials into the sample before the rotating step. This step may be accomplished by pressing the materials against the sample and may also include applying a film to the surface of the materials and tread. The film can be pressed against the materials and into the tread using e.g., a roller. The method may include removing excess material from the surface of the sample. The tread sample may be cleaned before loading with the materials in order to remove any foreign substance or materials left over from a previous evaluation.

A variety of materials may used for evaluating the tire tread. For example, the method may include mixing the materials from two or more of the group of components that includes water, sand, clay, and silt. Other compositions may also be used as well.

The method may also include the steps of measuring the speed at which the sample is rotated; recording, as a function of time, the speed at which the sample is rotated; and/or rotating the sample at a predetermined rpm (revolutions per minute) profile.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Figure 1:
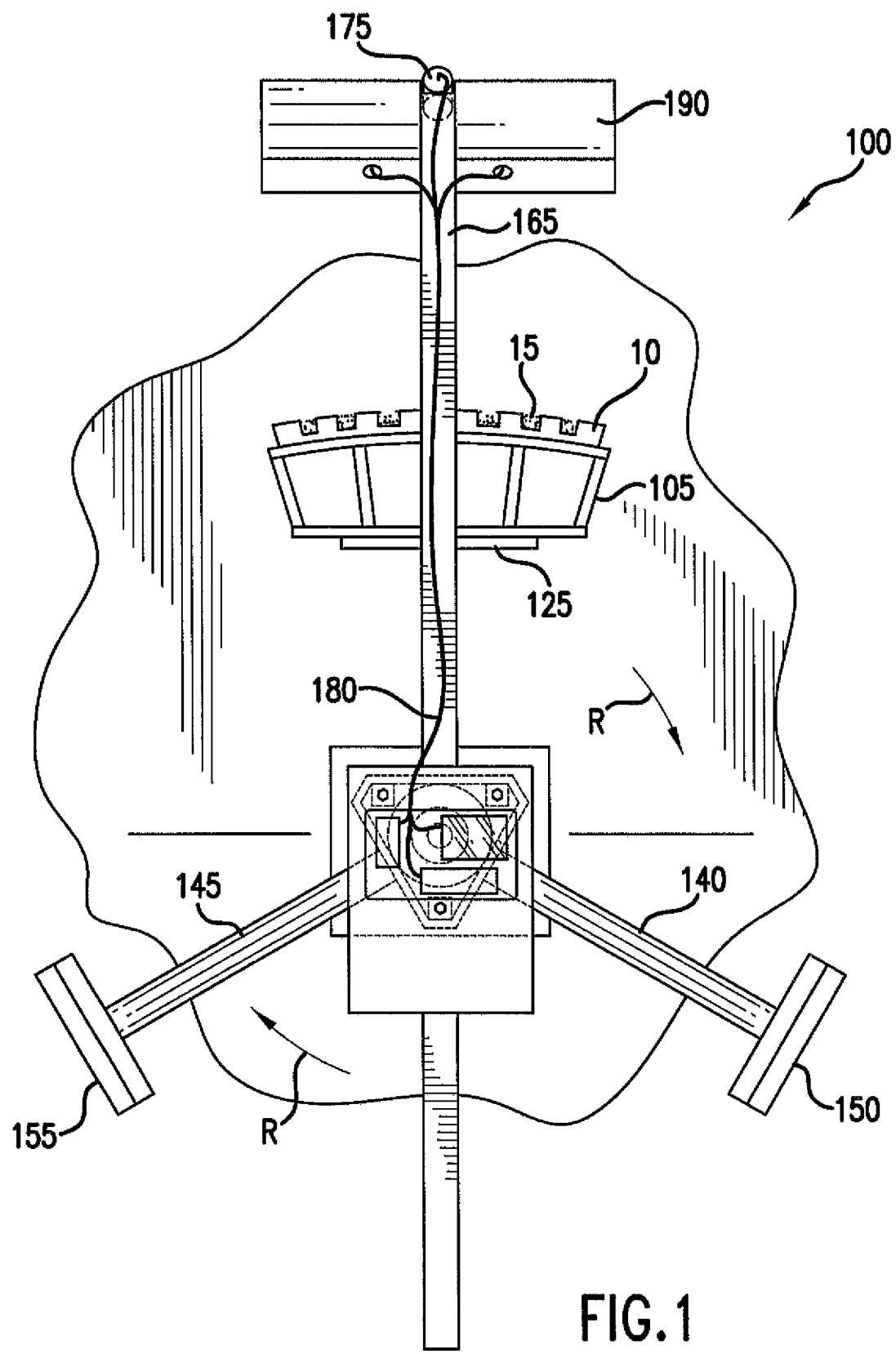
FIG. 1 illustrates a perspective view of the front of an exemplary embodiment of an apparatus that may be used with the present invention to test the self-cleaning ability of a sample tread portion.

The present invention evaluates the ability of a tire to clean its tread. More particularly, the present invention provides an exemplary apparatus and method for evaluating the ability of a tire to eject materials such as e.g., mud from its tread during use. For purposes of describing the invention, reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used with another embodiment to yield a still further embodiment. Thus, it is intended that the present invention covers such modifications and variations as come within the scope of the appended claims and their equivalents.

Figure 4:
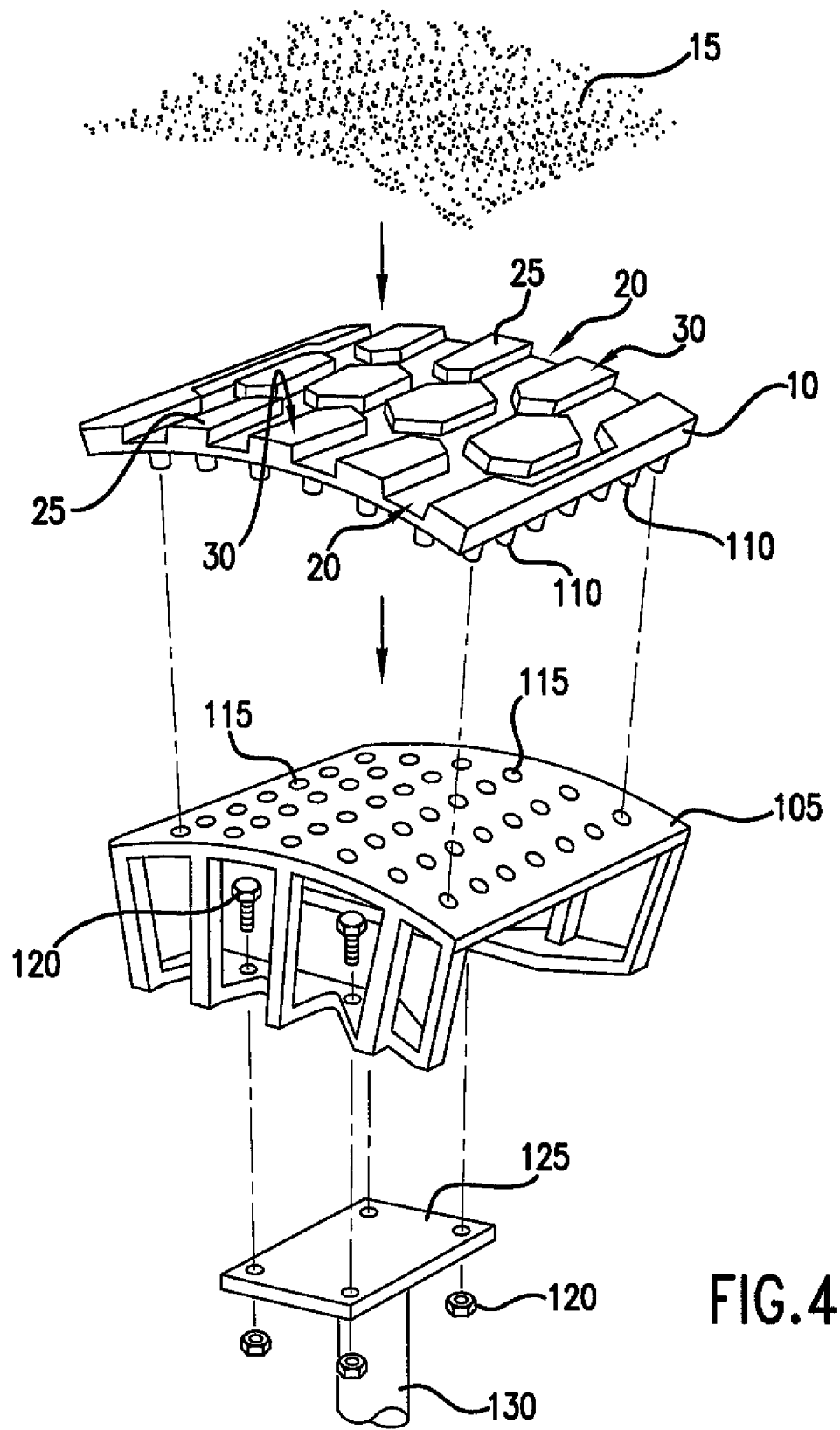
FIG. 4 illustrates the loading of a sample with materials and the mounting of the sample onto the mount.

In one exemplary aspect of the present invention, a tread sample 10 is provided as best shown in FIG. 4. Sample 10 provides a portion of a tread pattern for which testing of the pattern's ability to self-clean is desired. By way of example, sample 10 may represent one pitch of the proposed tread pattern. Sample 10 may contain a completely new pattern or may include modifications of an existing pattern for which improvements in traction are being targeted. Sample 10 is provided by way of example only and larger or smaller portions of the overall tread pattern may be used for testing.

As shown in FIG. 4, sample 10 is loaded into a carriage 105. A plurality of pegs 110 on the non-tread side of sample 10 connect into multiple apertures 115 defined by carriage 105. Using fasteners 120, carriage 105 is attached to a mount 125 on apparatus 100 as will be further described. Pegs 110 and fasteners 120 are provided by way of example only. Other techniques may be used to configure tread sample 10 to be carried by mount 125. By way of example, sample 10 could be attached directly to mount 125 using bolts, hook and loop fasteners, and other attachment devices as well. Other techniques may also be used to attach sample 10 to carriage 105.

Figure 3:
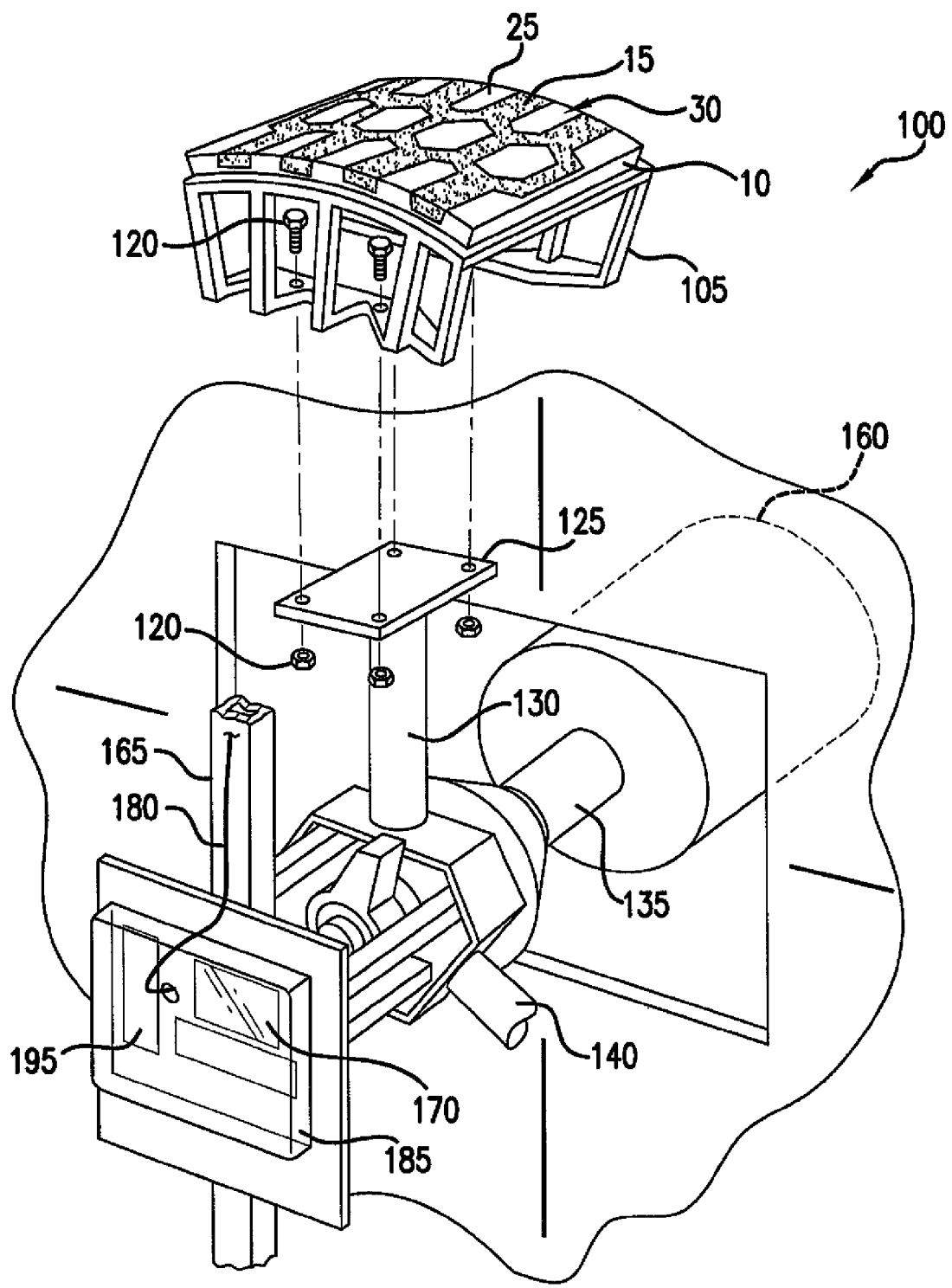
FIG. 3 is a partial perspective view of the embodiment of FIG. 1 illustrating the positioning of a tread sample portion upon the mount of the apparatus.

After cleaning to remove any residue from e.g., prior evaluations, sample 10 is loaded with materials 15. More particularly, as best shown in FIGS. 3 and 4, the grooves 20 or voids in tread sample 10 are filled with materials 15, which are intended to be representative of the conditions a tire might encounter in off road operation. A variety of materials 15 may be used for testing. For example, materials such as clay, sand, and or silt may be combined with water to create a paste or "mud" that is loaded into the grooves 20 of tread sample 10. Other ingredients and mixtures thereof may also be used for materials 15. Preferably, the same composition is used for materials 15 when comparing different tread samples in order to prevent variations in the composition from affecting the results.

Sample 10 is loaded by pressing materials 15 into grooves 20 between tread blocks 25. Pressing helps to remove air pockets and bubbles from materials 15. One technique that may be used is to spread the materials 15 into the grooves 20 and over blocks 25 using a trowel to create a layer of materials 15 that is about 3 to 5 mm higher than blocks 25. Next, a thin film of material—such as e.g., freezer paper or a plastic coated Kraft paper—is applied over the materials 15. A roller is then used to press against the paper and remove (or at least substantially reduce) the amount of air pockets and bubbles. Preferably, the roller is placed along the middle of sample 10 and then worked towards the edge of sample 10. The paper is removed and another layer of materials 15 is applied over sample 10 at thickness of about 3 to 5 mm higher than blocks 25. The paper is replaced and the entire process is repeated for a total of three times in an effort to remove all air pockets and bubbles.

Finally, an additional thin film of materials 15 is applied over sample 10. A flat edge, such as e.g., a squeegee, is now used to level the surface, fill in irregularities caused by removal of the paper, and remove materials 15 from surfaces 30 of blocks 25. The removal of materials from surfaces 30 helps maximize the visual difference in appearance between materials 15 and blocks 25 so as to enhance image capture by camera eye 175 as further described below.

Figure 2:
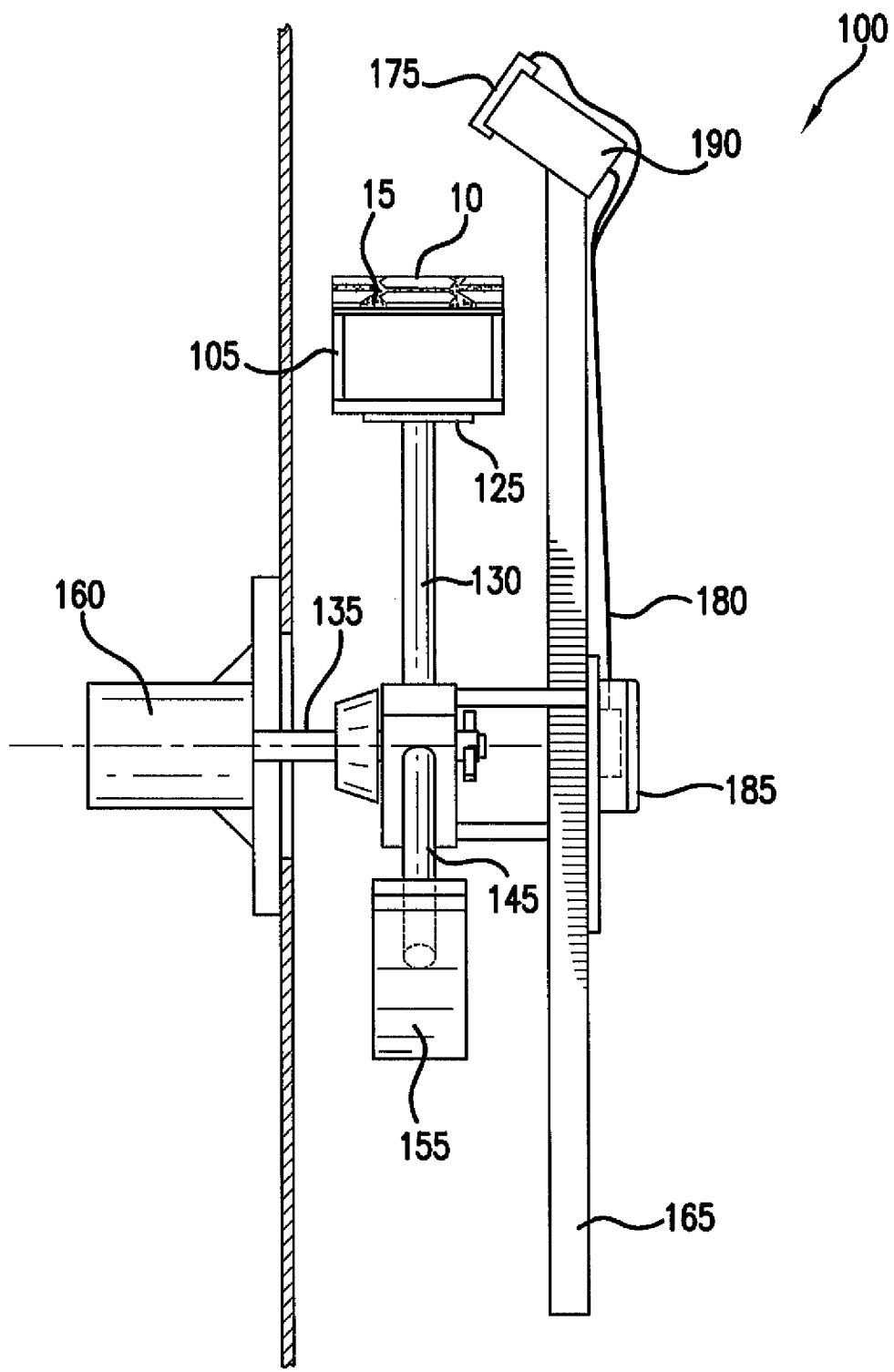
FIG. 2 illustrates a side view of the exemplary embodiment of FIG. 1.

FIGS. 1 through 3 provide views of an exemplary embodiment of an apparatus 100 that may be used with the present invention to test the self-cleaning ability of tread sample 10. As previously described, using carriage 105, tread sample 10 is connected to the mount 125. In turn, mount 125 is attached to an arm 130 carried upon a shaft 135. Arms 140 and 145 are also carried by shaft 135. Weights 150 and 155 are carried by arms 140 and 145 and counter the weight of tread sample 10, carriage 105 and mount 125 so that rotation as indicated by arrows R will be balanced about shaft 135 (the direction of rotation can be reversed from that shown by arrows R). Weights 150 and 155 can also be adjusted for e.g., variations in the size of tread sample 10 and/or carriage 105.

Shaft 135 is driven by motor 160. Preferably motor 160 is electrically powered and is regulated by a controller (not shown) that is in communication with motor 160 and is configured for controlling the speed of motor 160. More specifically, the controller can preferably determine the rate of acceleration, deceleration, and speed of motor 160 so as to create the desired rpm (revolutions per minute) profile. The controller may also provide the ability to measure the speed of rotation of shaft 135 or a separate speed sensor may be provided for this purpose.

As stated, the controller can be used during a tread sample evaluation to create a selected rpm profile for shaft 135 and, consequently, the rpm profile of arms 130, 140, and 145. The rotation of arm 130 creates centrifugal forces on materials 15 loaded into sample 10. As will be understood, the magnitude of the rpm for shaft 135 will determine the amount of centrifugal force acting upon materials 15. Therefore, by controlling the speed of rotation, the duration and amount of centrifugal forces experienced by materials 15 during the evaluation of sample 10 can be controlled. In addition, if desired, the amount of centrifugal acceleration at any given time during the evaluation can also be calculated from the rpm and length of arm 130 as will be understood by those skilled in the art.

Camera 170 is located within a protective equipment box 185, which shields the camera from any materials 15 that are ejected from tread sample 10 during rotation. Camera 170 is connected to a camera eye 175 by wiring harness 180. Eye 175 is positioned at the end of support member 165. More importantly, eye 175 is oriented towards sample 10 and, along with camera 170, rotates in synchronization with sample 10 to record the effect of the centrifugal forces on materials 15.

Camera 170 may be selected from a variety of types and configurations to facilitate the capture of visual information during the rotation of tread sample 10. By way of example only, camera 170 may be a digital camera configured to capture multiple images during rotation. The number of images and the time between successive images can be adjusted to determine the amount of information that is captured. As another example, a "video" camera may be used to record the rotation of tread sample 10 and video cameras of different recording speeds may be used depending upon the level of visual definition desired during review of the recording. Accordingly, as used herein, "record" or "recording images" includes the use of a multiple different cameras and media types for visually capturing the response of materials 15 to the centrifugal forces that will be created during the rotation of sample 10.

To ensure proper illumination of sample 10 and minimize the effects of other light sources during testing, apparatus 100 includes a light source 190 that also rotates in synchronization with sample 10 and camera 170. Light source 190 is connected by wiring harness 180 to a power supply (e.g., batteries) 195 in equipment box 185. By way of example, light source 190 may be constructed from a plurality of light emitting diodes (LEDs), which generally provide the lumens needed for capturing images using camera 170 while minimizing power consumption.

Accordingly, after loading with materials 15 and attaching to mount 125, tread sample 10 is rotated along a predetermined rpm profile to submit materials 15 to centrifugal force. Camera 170 is activated before rotation begins, remains operating during rotation, and is turned off after all materials 15 have been ejected or the rotation of sample 10 is stopped. In one exemplary aspect of the invention, sample 10 is rotated until all, or at least a portion, of the loaded materials 15 are ejected during rotation. Using camera 170, the rotation of sample 10 is recorded from e.g., the time rotation begins until the time rotation is ended. The time interval allowed for rotating sample 10 can vary. Preferably, the time interval for the rotation of sample 10 allows for all materials 15 to be ejected from the sample or at least until no more materials 15 are being ejected from the sample for a selected rpm profile. The time required for such events depends on several factors including e.g., the rpm, the composition of materials 15, and the tread pattern of tread sample 10. By holding all other variables constant or unchanged while varying only the tread pattern, the effect of differences in tread pattern for sample 10 may be studied.

Accordingly, apparatus 100 is useful in testing the ability of various tread patterns to self-clean. More specifically, tread samples 10 having different patterns can each be loaded onto apparatus 100. Each sample is then subjected to the same rpm profile—i.e. the same time interval for rotation with the same acceleration and speeds over a given time interval. By way of example, an rpm profile might include a linear acceleration profile where the rotational speed of the sample 10 is changed from 0 to 325 rpm over a six minute time period. However, other rpm profiles of different speeds and accelerations may also be used.

The rotation of each sample 10 through the selected rpm profile is recorded using camera 170. The resulting images can then be compared to determine the impact of differences in the tread patterns among samples 10. For example, the times at which materials 15 are first observed ejecting from the samples 10 during rotation may be compared. The times at which all or a certain percentage of materials has been ejected from the samples 10 may also be compared. As such, apparatus 100 provides for determining the effect that differences in tread patterns can have on the self-cleaning ability of a tire. In addition, apparatus 100 has economic advantages for design development as it allows for tread pattern testing with only a predetermined portion of the tread and without manufacture of a complete tire for off road testing. Apparatus 100 can be used to test new patterns and guide the development of new patterns by exploring whether modifications improve the self-cleaning ability of the new pattern. Similarly, apparatus 100 can be used to guide the modifications of existing tread patterns in order to improve their self-cleaning ability.

While the present subject matter has been described in detail with respect to specific exemplary embodiments and methods thereof, it will be appreciated that those skilled in the art, upon attaining an understanding of the foregoing, may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art using the teachings disclosed herein.

What is claimed is:

1. A device for evaluating the removal of materials from a tire tread, the device comprising:
   a mount configured for carrying a tread portion;
   a motor connected with said mount and adapted to rotate said mount about an axis of rotation so as to create centrifugal forces on the tread portion and materials in the tread portion;
   a plurality of arms connected with said motor and extending radially outward from the motor, said mount attached to an end of one of said plurality of arms, and wherein said arms and mount are configured to rotate in synchronization with each other about the axis of rotation; and
   a camera positioned to rotate in synchronization with said mount and configured to record images of the tread portion as said mount and tread portion are rotated.

2. A device for evaluating the removal of materials from a tire tread as in claim 1, further comprising a controller in communication with said motor and configured for controlling the speed of rotation of said mount.

3. A device for evaluating the removal of materials from a tire tread as in claim 1, further comprising a light source positioned adjacent to said mount for providing illumination of the tread portion.

4. A device for evaluating the removal of materials from a tire tread as in claim 1, further comprising a camera eye positioned adjacent to said mount and directed towards the mount, said camera eye connected to said camera and configured to rotate in synchronization with said mount.

5. A device for evaluating the removal of materials from a tire tread as in claim 1, wherein said arms further comprise a plurality of weights configured to balance rotation of the tread portion by the motor.

6. A device for evaluating the removal of materials from a tire tread as in claim 1, further comprising speed sensor for determining the speed at which said mount is rotated.

7. A device for evaluating the removal of materials from a tire tread as in claim 1, further comprising a carriage for receipt of the tread portion, the carriage being configured for removable connection with said mount.

8. A method for evaluating the removal of materials from a tire tread, the method comprising the steps of:

loading a sample portion of the tread onto a testing device;
placing materials into the sample;
rotating the sample portion at a predetermined rate about an axis of rotation using the testing device;
recording images of the sample portion during said rotating step using an image capture device that rotates in synchronization with the sample portion; and
ejecting the materials from the sample portion by centrifugal force during said rotating step.

9. A method for evaluating the removal of materials from a tire tread as in claim 8, further comprising the step of counter balancing the sample portion of the tread during said step of rotating.

10. A method for evaluating the removal of materials from a tire tread as in claim 9, wherein said placing step further comprises pressing the materials against the sample.

11. A method for evaluating the removal of materials from a tire tread as in claim 10, wherein said pressing step further comprises applying a film to the surface of the materials and tread.

12. A method for evaluating the removal of materials from a tire tread as in claim 10, wherein said placing step further comprises removing excess material from the surface of the sample.

13. A method for evaluating the removal of materials from as tire tread as in claim 9, further comprising the step of mixing the materials from two or more of the group of components that includes water, sand, clay, and silt.

14. A method for evaluating the removal of materials from a tire tread as in claim 8, further comprising the step of measuring the speed at which the sample is rotated.

15. A method for evaluating the removal of materials from a tire tread as in claim 14, further comprising the step of recording, as a function of time, the speed at which the sample is rotated.

16. A method for evaluating the removal of materials from a tire tread as in claim 8, wherein the predetermined rate of said rotating step comprises a predetermined rpm profile.

17. A method for evaluating the removal of materials from a tire tread as in claim 8, further comprising the step of cleaning the sample of the tread portion before said rotating step.

18. A method for evaluating the removal of materials from a tire tread as in claim 8, further comprising the step of modifying the tread pattern used on the tread using the images from said recording step.

* * * * *